(12) United States Patent
Sen

(10) Patent No.: US 9,901,596 B2
(45) Date of Patent: Feb. 27, 2018

(54) REGULATION OF BODY WEIGHT GAIN BY USING DIBENZO-ALPHA-PYRONES

(71) Applicant: Natreon, Inc., New Brunswick, NJ (US)

(72) Inventor: Chandan K. Sen, Columbus, OH (US)

(73) Assignee: Natreon, Inc., New Brunswick, NJ (US)

( * ) Notice: Subject to any disclaimer, the term of this patent is extended or adjusted under 35 U.S.C. 154(b) by 0 days.

(21) Appl. No.: 14/917,721

(22) PCT Filed: Sep. 9, 2014

(86) PCT No.: PCT/US2014/054798
§ 371 (c)(1),
(2) Date: Mar. 9, 2016

(87) PCT Pub. No.: WO2015/035391
PCT Pub. Date: Mar. 12, 2015

(65) Prior Publication Data
US 2016/0213644 A1    Jul. 28, 2016

Related U.S. Application Data

(60) Provisional application No. 61/875,513, filed on Sep. 9, 2013.

(51) Int. Cl.
*A61K 35/04*   (2006.01)
*A61K 36/09*   (2006.01)
*A61K 31/37*   (2006.01)
*A61K 35/66*   (2015.01)

(52) U.S. Cl.
CPC .............. *A61K 35/04* (2013.01); *A61K 31/37* (2013.01); *A61K 35/66* (2013.01); *A61K 36/09* (2013.01)

(58) Field of Classification Search
CPC .............................. A61K 31/366; A61K 31/37
USPC ....................................................... 514/455
See application file for complete search history.

(56) References Cited

U.S. PATENT DOCUMENTS

2008/0234367 A1   9/2008   Washburn et al.
2012/0164243 A1   6/2012   Rinsch et al.

OTHER PUBLICATIONS

Roy, S., et al., Characterization of a preclinical model of chronic ischemic wound. Physiol Genomics. May 13, 2009;37(3):211-24.
Roy, S., et al., Characterization of the acute temporal changes in excisional murine cutaneous wound inflammation by screening of the wound-edge transcriptome. Physiol Genomics. Jul. 15, 2008;34(2):162-84.
Roy, S., et al., Transcriptome-wide analysis of blood vessels laser captured from human skin and chronic wound-edge issue. Proc Natl Acad Sci U S A. Sep. 4, 2007;104(36):14472-7.

*Primary Examiner* — San Ming R Hui
(74) *Attorney, Agent, or Firm* — Amin Talati Upadhye LLP; George M. Carrera, Jr.

(57) ABSTRACT

A method of using dibenzo-alpha-pyrones (DBPs) is provided wherein a subject is administered one or more of the aforementioned resulting in decreased body weight gain. In an embodiment, a 3-OH-DBP, 3,8-(OH)$_2$-DBP, or a combination thereof is administered to an individual to control body weight gain.

16 Claims, 7 Drawing Sheets

Effect of Shilajit and 3,8-(OH)$_2$-DBP Supplementation on Weight Gain in C57/BL6 Mice on Standard Laboratory Diet - Study 1

Effect of Shilajit and 3,8-(OH)$_2$-DBP Supplementation on Weight Gain in C57/BL6 Mice on Standard Laboratory Diet – Study 1

Genes up regulated in group supplemented with 3,8-(OH)$_2$-DBP
Top 20 based on fold change

| Gene Symbol | Gene Title | mean | p value |
| --- | --- | --- | --- |
| 1100001G20R/k | RIKEN cDNA 1100001G20 gene | 1.634 | 0.029 |
| Cod c80 | coiled-coil domain containing 80 | 1.625 | 0.023 |
| Col1a1 | collagen, type I, alpha 1 | 1.557 | 0.037 |
| Cyr61 | cysteine rich protein 61 | 1.544 | 0.008 |
| Cyr61 | cysteine rich protein 61 | 1.54 | 0.008 |
| LOC100047252/ | phosphoserine aminotransferase-like /// phosphoserin | 1.452 | 0.016 |
| Fscn1 | fascin homolog 1, actin bundling protein (strongyloc | 1.447 | 0.018 |
| Dusp 10 | dual specificity phosphatase 10 | 1.442 | 0.029 |
| LOC100047252/ | phosphoserine aminotransferase-like /// phosphoserin | 1.41 | 0.034 |
| Apcd d1 | adenomastosis polyposis coli down-regulated 1 | 1.401 | 0.013 |
| Vim | vimentin | 1.398 | 0.026 |
| Mylk4 | myosin light chain kinase family, member 4 | 1.387 | 0.03 |
| Dusp 10 | dual specificity phosphatase 10 | 1.341 | 0.025 |
| Sf3a2 | splicing factor 3a, subunit 2 | 1.335 | 0.029 |
| Id4 | inhibitor of DNA binding 4 | 1.332 | 0.036 |
| Pltp | phosolipid transfer protein | 1.332 | 0.03 |
| 2700081O15R/k | RIKEN cDNA 2700081O15 gene | 1.33 | 0.014 |
| Sparc | secreted acidic cysteine rich glycoprotein | 1.328 | 0.033 |
| Ccna2 | cyclin A2 | 1.138 | 0.034 |
| 5430421817 | uncharacterized protein 5430421817 | 1.315 | 0.008 |

FIG. 4

Genes down regulated in group supplemented with 3,8-(OH)$_2$-DBP
Top 20 based on fold change

| Gene Symbol | Gene Title | mean | p value |
|---|---|---|---|
| Slc12a6 | solute carrier family 12, member 6 | -2.199 | 0.025 |
| Tmed7 | Transmembrane emp24 protein transport do | -2.192 | 0.027 |
| Rab2a | RAB2A, member RAS oncogene family | -2.13 | 0.041 |
| 1810014B01R/k | RIKEN cDNA 1810014B01 gene | -2.117 | 0.01 |
| 4930429F24R/k | RIKEN cDNA 4930429F24 gene | -1.99 | 0.045 |
| Nudt 21 | nudix (nucleoside diphosphate linked moiety | -1.975 | 0.009 |
| Tm2d1 | TM2 domain containing 1 | -1.77 | 0.029 |
| Tes 3-ps | testis derived transcript 3, pseudogene | -1.7 | 0.013 |
| Nfil3 | nuclear factor, interleukin 3, regulated | -1.687 | 0.039 |
| Zfp260 | zinc finger protein 260 | -1.657 | 0.024 |
| Gn pn at 1 | glucosamine-phosphate N-acetayltransferase | -1.652 | 0.034 |
| Nol7 | nucleolar protein 7 | -1.582 | 0.036 |
| Zscan21 | zinc finger and SCAN domain containing 21 | -1.55 | 0.023 |
| Pim1 | proviral integration site 1 | -1.488 | 0.014 |
| P pp 2r2d | Protein phosphatase 2, regulatory subunit B | -1.486 | 0.048 |
| Slc38a4 | solute carrier family 38, member 4 | -1.476 | 0.045 |
| Slc25a36 | solute carrier family 25, member 36 | -1.474 | 0.03 |
| Ccl9 | chemokine (C-C motif) ligand 9 | -1.471 | 0.009 |
| B230337E12R/k | RIKEN cDNA B230337E12 gene | -1.47 | 0.024 |
| Gramd4 | GRAM domain containing 4 | -1.47 | 0.009 |

FIG. 5

Genes up regulated in both groups, i.e., supplemented with
3,8-(OH)$_2$-DBP or Shilajit
Top 20 based on fold change

| Gene Symbol | Gene Title | mean | p value |
|---|---|---|---|
| Lep | leptin | 2.423 | 0.085 |
| Tmem45b | transmembrane protein 45b | 2.101 | 0.069 |
| Mid1ip1 | Mid 1 interacting protein 1 (gastrulation specific G12-like (zeb | 1.925 | 0.02 |
| Agpat2 | 1-acylglycerol-3-phosphate 0-acyltransferase 2 (lysophosphatid | 1.829 | 0.086 |
| Nnat | neuronatin | 1.809 | 0.056 |
| Aoc3 | amine oxidase, copper containing 3 | 1.744 | 0.051 |
| Per2 | period homolog 2 (0 rosophilia) | 1.723 | 0.086 |
| Rbp4 | retinol binding protein 4, plasma | 1.709 | 0.086 |
| Cebpa | CCAAT/enhancer binding protein (C/EBP), alpha | 1.709 | 0.09 |
| Scd1 | stearoyl-Coenzyme A desaturase 1 | 1.705 | 0.084 |
| Cd1d1 | CD1d1 antigen | 1.698 | 0.053 |
| Cd1d1 | CD1d1 antigen | 1.69 | 0.073 |
| Slc1a5 | solute carrier family 1 (neutral amino acid transporter), membe | 1.687 | 0.056 |
| Npr3 | natriuretic peptide receptor 3 | 1.687 | 0.116 |
| Acp5 | acid phosphatase 5, tartrate resistant | 1.67 | 0.076 |
| Dbp | D site albumin promoter binding protein | 1.625 | 0.091 |
| Zfp503 | zinc finger protein 503 | 1.578 | 0.022 |
| Zfp503 | zinc finger protein 503 | 1.577 | 0.034 |
| Sncg | synuclein, gamma | 1.561 | 0.112 |
| G0s2 | G0/G1 switch gene 2 | 1.559 | 0.052 |

FIG. 6

Genes down regulated in both groups, i.e., supplemented with
3,8-(OH)$_2$-DBP or Shilajit
Top 20 based on fold change

| Gene Symbol | Gene Title | mean | p value |
|---|---|---|---|
| Tmed7 | Transmembrane emp 24 protein transport do | -1.86279 | 0.008381 |
| Slc12a6 | solute carrier family 12, member 6 | -1.8604 | 0.005502 |
| 1810014B01R/k | RIKEN cDNA 1810014B01 gene | -1.82161 | 0.001617 |
| 4930429F24R/k | RIKEN cDNA 4930429F24 gene | -1.74675 | 0.010506 |
| Tes3-ps | testis derived transcript 3, pseudogene | -1.58894 | 0.000633 |
| Hd ac9 /// | histone deacetylase 9 /// histone deacetylase | -1.55665 | 0.003186 |
| Klf 10 | Kruppel-like factor 10 | -1.55567 | 0.021268 |
| Zfp462 | zinc finger protein 462 | -1.48282 | 0.01452 |
| Gn p nat1 | glucosamine-phosphate N-acetyltransferase | -1.46627 | 0.012736 |
| P im 1 | proviral integration site 1 | -1.44609 | 0.012581 |
| Zscan 21 | zinc finger and SCAN domain containing 21 | -1.42369 | 0.01326 |
| Gpsm1 | G-protein signalling modulator 1 (AGS3-like | -1.38416 | 0.010451 |
| Igfb p3 | insulin-like growth factor binding protein 3 | -1.3815 | 0.00717 |
| Gramd4 | GRAM domain containing 4 | -1.38072 | 0.001741 |
| Lrrc8c | leucine rich repeat containing 8 family, mem | -1.37862 | 0.001427 |
| P igf | phosphatidylinositol glycan anchor biosynth | -1.35041 | 0.015473 |
| Esrp2 | epithelial splicing regulatory protein 2 | -1.3455 | 0.00113 |
| R arb | retinoic acid receptor, beta | -1.33744 | 0.003875 |
| Abtb 2 | ankyrin repeat and BTB (P OZ) domain cont | -1.33637 | 0.019818 |
| R bm 12 | RNA binding motif protein 12 | -1.32638 | 1.95E-05 |

FIG. 7

REGULATION OF BODY WEIGHT GAIN BY USING DIBENZO-ALPHA-PYRONES

This application is a U.S. National Stage application under 35 U.S.C. § 371 of International Application No. PCT/US2014/054798, filed on Sep. 9, 2014, which claims the benefit of earlier filed U.S. Provisional Application No. 61/875,513, filed on Sep. 9, 2013, each of which are hereby incorporated by reference herein.

FIELD OF THE INVENTION

The present invention relates to promoting loss of body weight and/or treating or preventing excess body weight gain through the use of dibenzo-alpha-pyrones (DBPs), the chemical building blocks of fulvic acids in Shilajit.

BACKGROUND

Shilajit is composed of rock humus, rock minerals and organic substances that have been compressed by layers of rock mixed with marine organisms and microbial metabolites. It oozes out of the rocks in the Himalayas at higher altitudes ranging from 1000-5000 meters as black mass and is regarded as a maharasa (super-vitalizer) in Ayurveda, the traditional Indian system of medicine, dating back to 3500 B.C. Shilajit contains fulvic acids as the main components along with dibenzo-α-pyrones ("DBPs") and dibenzo-α-pyrone chromoproteins.

Fulvic acid complex, derived from shilajit, is an assembly of naturally occurring low and medium molecular weight compounds comprising oxygenated dibenzo-alpha-pyrones (DBPs), both in reduced as well as in oxidized form, as the core nucleus, and acylated DBPs and lipids as partial structural units, along with fulvic acids ("FAs"). Fulvic acid complex material derived from alluvial sources lack DBPs instead, the core nucleus of alluvial fulvic acid is comprised of benzoic acid.

Thus, the active constituents of shilajit contain dibenzo-alpha-pyrones and related metabolites, small peptides (constituting non-protein amino acids), some lipids, and carrier molecules (fulvic acids). See, Ghosal, S., et al., "Shilajit Part 1—Chemical constituents," *J. Pharm. Sci.* (1976) 65:772-3; Ghosal, S., et al., "Shilajit Part 7—Chemistry of Shilajit, an immunomodulatory ayurvedic rasayana," *Pure Appl. Chem.* (IUPAC) (1990) 62:1285-8; Ghosal, S., et al., "The core structure of Shilajit humus," *Soil Biol. Biochem.* (1992) 23:673-80; and U.S. Pat. Nos. 6,440,436 and 6,869,612 (and references cited therein); all hereby incorporated by reference herein.

Shilajit (e.g., PrimaVie®) finds extensive use in Ayurveda, for diverse clinical conditions. For centuries, people living in the isolated villages in Himalayas and adjoining regions have used Shilajit alone, or in combination with, other plant remedies to prevent and combat problems with diabetes (Tiwari, V. P., et al., "An interpretation of Ayurvedica findings on Shilajit," *J. Res. Indigenous Med.* (1973) 8:57). Moreover being an antioxidant it will prevent damage to the pancreatic islet cell induced by the cytotoxic oxygen radicals (Bhattacharya S. K., "Shilajit attenuates streptozotocin induced diabetes mellitus and decrease in pancreatic islet superoxide dismutase activity in rats," *Phytother. Res.* (1995) 9:41-4; Bhattacharya S. K., "Effects of Shilajit on biogenic free radicals," *Phytother. Res.* (1995) 9:56-9; and Ghosal, S., et al., "Interaction of Shilajit with biogenic free radicals," *Indian J. Chem.* (1995) 34B:596-602). It has been proposed that the derangement of glucose, fat and protein metabolism during diabetes, results into the development of hyperlipidemia. In one study, Shilajit produced significant beneficial effects in lipid profile in rats (Trivedi N. A., et al., "Effect of Shilajit on blood glucose and lipid profile in alloxan-induced diabetic rats," *Indian J. Pharmacol.* (2004) 36(6):373-376).

As discussed, shilajit has been used to treat various ailments. It is also recommended as a performance enhancer. Fulvic acids (FAs) are reported to elicit many important roles in biological systems of plants, in animals as well as humans, including: (a) improvement of bioavailability of minerals and nutrients, (b) serve as electrolytes, (c) detoxification of toxic substances including heavy metals, (d) perform as antioxidants, and (e) improvement of immune function.

Furthermore, dibenzo-α-pyrones have been hypothesized to participate in the electron transport inside the mitochondria, thus facilitating production of more ATP, leading to increased energy.

Thus, it would be desirable to determine which genes in the body are affected by DBPs as well as Shilajit so that a clear understanding of their pharmacological role, especially related to body weight gain or loss, can be ascertained.

SUMMARY OF THE INVENTION

An objective of the present invention is to develop a method of using DBP compositions for promoting or producing loss of (excess) body weight and/or treating or preventing excess body weight gain in obese mammals (e.g., with Type 2 diabetes mellitus) as well as in healthy mammals.

In one embodiment, a method for treating or preventing body weight gain is provided, comprising identifying a mammal in need of such treatment experiencing weight gain; and administering to the mammal in need of such treatment an effective amount of a compound selected from the group consisting of 3-hydroxy-dibenzo-alpha-pyrone, 3,8-dihydroxy-dibenzo-alpha-pyrone, and mixtures thereof, wherein body weight gain is decreased compared to body weight gain prior to treatment.

In another embodiment, a method for producing loss of excess body weight in a mammal is provided comprising administering to the mammal in need of such treatment an effective amount of a compound selected from the group consisting of 3-hydroxy-dibenzo-alpha-pyrone, 3,8-dihydroxy-dibenzo-alpha-pyrone, and mixtures thereof, wherein body weight is decreased.

BRIEF DESCRIPTION OF THE DRAWINGS

FIG. 2 depicts the effect of supplementation with DBPs on weight gain in mice on a high fat diet in Study 3.

FIG. 4 depicts genes up-regulated in mice treated with 3,8-(OH)$_2$-DBP.

FIG. 5 depicts genes down-regulated in mice treated with 3,8-(OH)$_2$-DBP.

FIG. 6 depicts genes up-regulated in mice treated with 3,8-(OH)$_2$-DBP or Shilajit.

FIG. 7 depicts genes down-regulated in mice treated with 3,8-(OH)$_2$-DBP or Shilajit.

DETAILED DESCRIPTION

Figure 1:
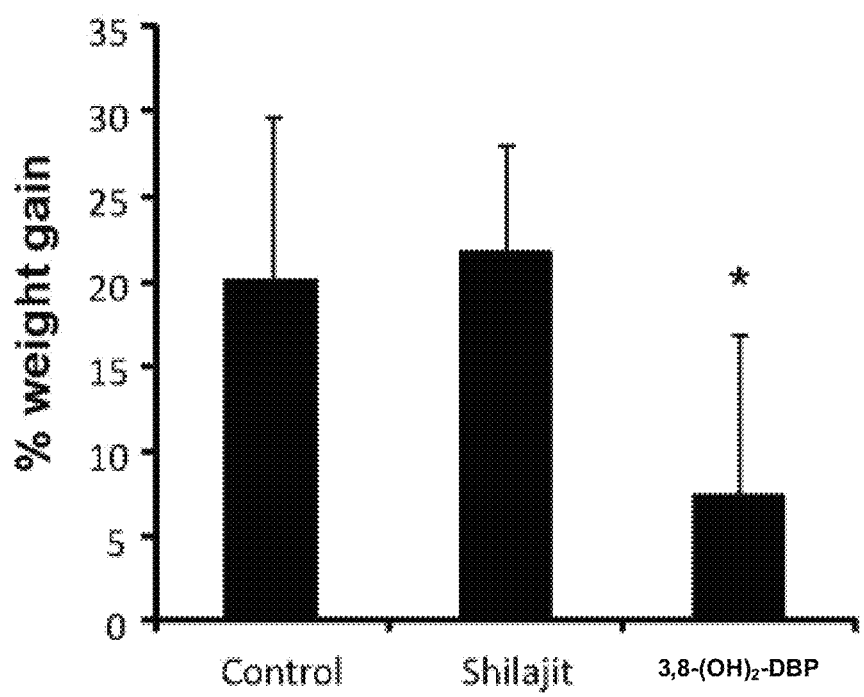
FIG. 1 depicts the effect of Shilajit and 3,8-(OH)$_2$-DBP supplementation on weight gain in mice on a standard laboratory diet in Study 1.

In one aspect, the present invention demonstrates the usefulness of 3-hydroxy-dibenzo-α-pyrone (3-OH-DBP), 3,8-dihydroxy-dibenzo-α-pyrone (3,8-(OH)$_2$-DBP), or combinations thereof in promoting or producing loss of excess body weight and/or treating or preventing excess body weight gain in obese mammals (e.g., with Type 2 diabetes mellitus) as well as in healthy mammals. As used herein, a mammal may include, but is not limited to, a human, a dog, a horse, or a cat.

In order to determine which genes are up regulated and which genes are down regulated by Shilajit and 3,8-dihydroxy-dibenzo-α-pyrone, an in-vivo gene expression study was carried out in mice and, during this study, it was discovered that the mice on 3,8-dihydroxy-dibenzo-α-pyrone treatment gained much less weight than the mice on placebo or Shilajit treatment. This first study was done on mice which were on standard laboratory diet. In order to confirm the results of this first study, a second study was done in mice, on standard laboratory diet again, this time including 3-hydroxy-dibenzo-α-pyrone also in the study. The second study confirmed the results with 3,8-dihydroxy-dibenzo-α-pyrone from the first study and showed that 3-hydroxy-dibenzo-α-pyrone may be working better than 3,8-dihydroxy-dibenzo-α-pyrone. A third in-vivo study was done in mice on high fat diet to determine if DBPs reduce weight gain in animals on high fat diet. The third study indicated that prevention of weight gain by DBPs might be slower in mice on high fat diet than in mice on standard laboratory diet. The findings in the above three studies are totally unexpected and form the basis of certain embodiments of this invention.

As described below, gene expression studies were carried out on C57/BL6 mice:

Study 1:

Materials Used: Shilajit (PrimaVie®, Natreon, Inc., New Brunswick, N.J.), a standardized dietary supplement ingredient extracted and processed from Shilajit bearing rocks, containing not less than about 50% by weight fulvic acids (FAs), at least about 10% by weight dibenzo-α-pyrone chromoproteins, and at least 0.3%, or more, by weight total dibenzo-α-pyrones (DBPs), 3-OH-DBP (99.0% purity, Natreon, Inc.), and 3,8-(OH)$_2$-DBP (99.0% purity, Natreon, Inc) were used.

Procedure for Studies in Mice:

Three groups of adult C57/BL6 mice (n=8) were intragastrically supplemented with purified Shilajit (PS), 3,8-dihydroxy-dibenzo-α-pyrone (3,8-(OH)$_2$-DBP) or placebo for 12 weeks. Body weight was measured every week. At the end of week 12, skeletal muscle tissue was harvested for gene profiling. Some tissue was stored for histology and HPLC analysis.

The control group of mice received DMSO in corn oil while the PS group received 100 mg of purified Shilajit/kg body weight of mice, dissolved in water and the DBP group received 10 mg of 3,8-(OH)$_2$-DBP/kg body weight of mice, dissolved in DMSO/corn oil.

At week 12, the following tissues were collected: heart, lung, liver, brain, muscles, adipose tissue, skeletal muscle (vastus lateralis) and whole blood.

Results: As shown in FIG. 1, a significant decrease in age-dependent gain in body weight was observed in mice of the 3,8-(OH)$_2$-DBP test group. The mice supplemented with 3,8-(OH)$_2$-DBP gained only about 7.5% weight in 90 days compared to the mice in Shilajit and placebo treated groups which gained over 20%, although all the groups were on the same standardized laboratory diet. This was a totally unexpected discovery.

In addition, mice supplemented with 3,8-dihydroxy-dibenzo-α-pyrone showed no overt signs of health compromise. Thus, the 3,8-dihydroxy dibenzo-α-pyrone seems to have the potential of controlling body weight gain without adversely affecting health.

Figure 2:
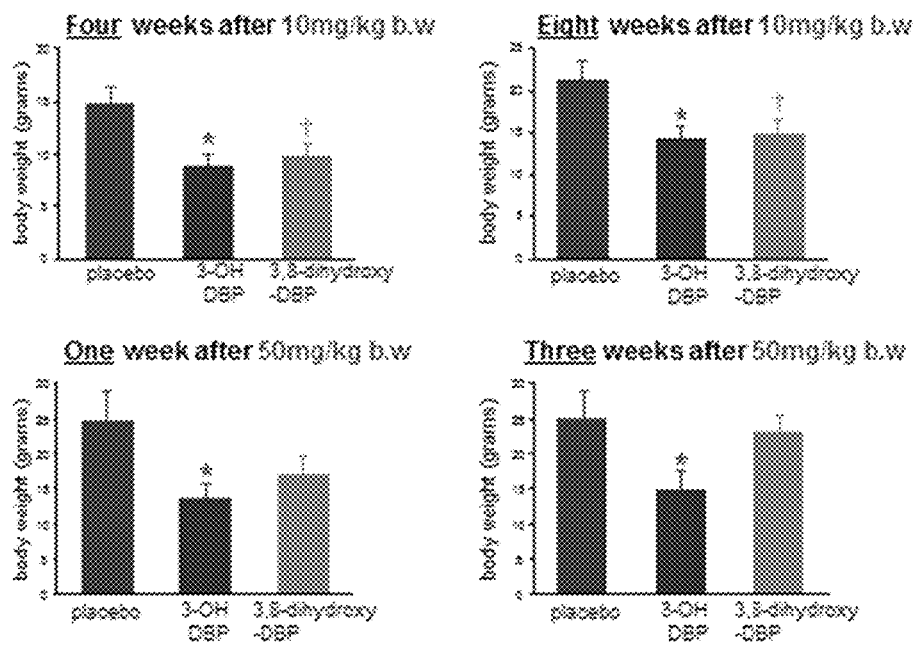
FIG. 2 depicts the effect of supplementation with DBPs on weight gain in mice on a standard laboratory diet in Study 2.

Since the results from Study 1 were totally unexpected, Study 2 was carried out in order to validate the results from Study 1 and also to determine if another bioactive of Shilajit, 3-hydroxy-dibenzo-α-pyrone, may have a similar beneficial effect on controlling body weight gain. Study 2 was carried out under similar experimental conditions as Study 1, using standard laboratory diet, except that a 10 mg/kg body weight dose was administered for the first 12 weeks and then the dose was increased to 50 mg/kg body weight from the 13$^{th}$ week through the 19$^{th}$ week. The primary purpose of increasing the dose is to find out if the response is dose proportional. As shown in FIG. 2, at 10 mg/kg b.w. dose, at four weeks there was about a 45% and 40% less gain in body weight in 3-OH-DBP and 3,8-(OH)$_2$-DBP groups respectively, while at 8 weeks there was about 50% less body weight gain in both the DBP groups. It is interesting to note that 3 weeks after increasing the dose of DBPs to 50 mg/kg b.w., 3-OH-DBP group still maintained about 45% less weight gain while the 3,8-(OH)$_2$-DBP group retained only about 10% less weight gain. Thus 3-OH-DBP may prove to be a better candidate to control weight gain than 3,8-(OH)$_2$-DBP. The secondary purpose of increasing the dose is to find out if increased dose is toxic. Different tissues were collected from the mice and toxicological examination will be conducted.

Figure 3:
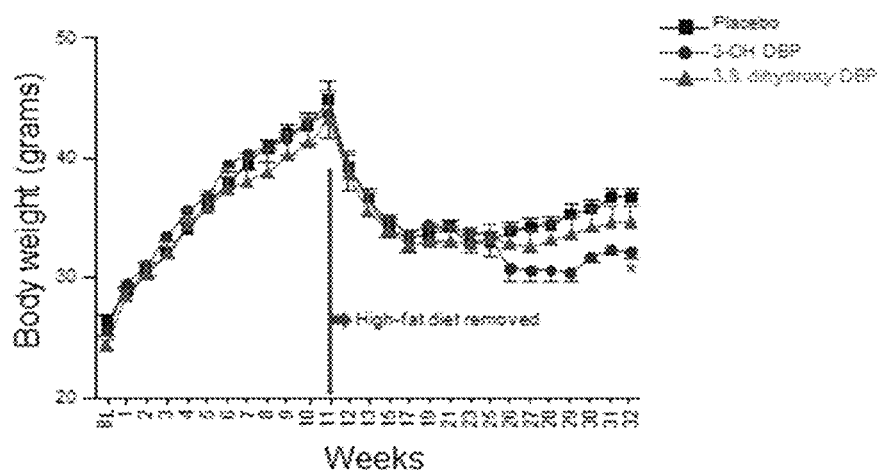

Since the Studies 1 and 2 were carried out with standard laboratory diet, it was imperative to do a study with high fat diet fed mice. Study 3 was conducted using such a diet (Bio-Serve Cat# 534282, 36% fat). After 11 weeks, the high fat diet was replaced with the standard laboratory diet. As shown in FIG. 3, neither DBP showed any difference in weight gain compared to placebo. However, starting at 14 weeks after switching to the standard laboratory diet, there is a trend in both the DBP groups for less weight gain compared to the placebo group. This trend is especially prominent with the 3-OH-DBP group. Thus, it is possible that the DBPs, especially the 3-OH-DBP, may have the potential to control body weight gain in individuals on fatty diet as well, though at a slower pace than in individuals on normal diet.

In accordance with these embodiments, it is further believed that the administration of DBPs to mammals, including humans, will result in decreased body weight gain in obese subjects (e.g., with Type 2 diabetes mellitus) as well as in healthy subjects. It is further believed that the administration of DBPs to mammals, including humans, will result in loss of body weight in obese subjects (e.g., with Type 2 diabetes mellitus) as well as in healthy subjects. In one embodiment, a useful daily dosage is from about 0.2 mg/kg body weight of the mammal to about 20 mg/kg body weight of the mammal.

Gene Expression Profiling using GeneChip® Assay

Affymetrix GeneChip® technology (Affymetrix, Santa Clara, Calif.) was used for transcriptome profiling in mouse skeletal muscle tissue. The gene chip studies were performed using standard techniques. The color of each enzyme/band in a given gene cluster array is calculated using a 3-point gradient of red (for the most up-regulated gene) to black (no expression) to green (most down-regulated gene). Thus, the intensity of the band indicate quantitative expression results, which are presented numerically in the Figures and Tables as "+/−" "fold change," red to green respectively. Gene chip assays were performed in accordance with the following references: Roy, S., Biswas, S., Khanna, S., Gordillo, G., Bergdall, V., Green, J., Marsh, C. B., Gould, L. J., Sen, C. K., "Characterization of a preclinical model of chronic ischemic wound," Physiol. Genomics (2009) May 13; 37(3):211-24; Roy, S., Khanna, S., Rink, C., Biswas, S., Sen, C. K., "Characterization of the acute temporal changes in excisional murine cutaneous wound inflammation by screening of the wound-edge transcriptome," Physiol. Genomics (2008) Jul. 15; 34(2):162-84; and Roy, S., Patel D, Khanna, S., Gordillo, G. M., Biswas, S., Friedman, A., Sen, C. K., "Transcriptome-wide analysis of blood vessels laser captured from human skin and chronic wound-edge tissue," Proc. Natl. Acad. Sci. USA (2007) Sep. 4; 104(36):14472-7; herein incorporated by reference.

FIG. 4 shows the top 20 genes up-regulated based on fold change in the mouse test group supplemented with 3,8-dihydroxy-dibenzo-α-pyrone; 1037 probes; 883 annotated used for analysis.

FIG. 5 shows the top 20 genes down-regulated based on fold change in the mouse test group supplemented with 3,8-dihydroxy dibenzo-α-pyrone; 1174 probes; 1135 annotated used for analysis.

FIG. 6 shows the top 20 genes up-regulated based on fold change in both mouse groups, i.e. supplemented with purified Shilajit (PS) or 3,8-dihydroxy dibenzo-α-pyrone; 221 probes; 208 annotated used for analysis.

FIG. 7 shows the top 20 genes down-regulated based on fold change in both mouse groups, i.e. supplemented with purified Shilajit (PS) or 3,8-dihydroxy dibenzo-α-pyrone; 231 probes; 225 annotated used for analysis.

Transcriptome profiling of tissues of mice in 3-OH-DBP groups is still pending.

As shown by the experiments above, DBP supplementation significantly blunted age-dependent gain of body weight in mice maintained under standard laboratory conditions. Results from analyses of skeletal muscle gene expression lead to the hypothesis that DBP supplementation is able to specifically influence specific gene expression pathways in the muscle. Although the specific significance of these pathways in attenuating age-related increase in body weight remains to be established, and without intending to be bound by theory, the efficacy of DBPs to manage body weight is clear. It is also clear that orally supplemented DBPs may influence gene expression pathways in tissues in vivo.

Additional studies are necessary to test whether DBP causes lipolysis thereby limiting gain of body weight. No overt signs of DBP toxicity were noted.

The product(s) of the present invention may be formulated into nutraceutical or pharmaceutical dosage forms comprising of tablets, capsules, powders, liquids, chews, gummies, transdermals, injectables, etc. using standard excipients and formulation techniques in the industry. The product of the subject invention may be administered to the mammal orally in solid dosage form or by parenteral, intramuscular, or transdermal administration.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

The invention claimed is:

1. A method for treating or preventing body weight gain comprising:
   identifying a mammal in need of such treatment experiencing weight gain; and
   administering to the mammal in need of such treatment an effective amount of 3 hydroxy-dibenzo-alpha-pyrone, wherein body weight gain is decreased compared to body weight gain prior to treatment;
   wherein 3-hydroxy-dibenzo-alpha-pyrone is present in a daily dosage of from about 0.2 mg/kg body weight of the mammal to about 20 mg/kg body weight of the mammal.

2. The method of claim 1, wherein 3-hydroxy-dibenzo-alpha-pyrone is administered orally, intramuscularly, parenterally or transdermally.

3. The method of claim 1, wherein the mammal is a human, a dog, a horse, or a cat.

4. The method of claim 1, wherein body weight gain is decreased at least about 5%.

5. The method of claim 1, wherein body weight gain is decreased at least about 10%.

6. A method for producing loss of excess body weight in a mammal comprising administering to the mammal in need of such treatment an effective amount of 3 hydroxy-dibenzo-alpha-pyrone, wherein body weight is decreased; wherein 3-hydroxy-dibenzo-alpha-pyrone is present in a daily dosage of from about 0.2 mg/kg body weight of the mammal to about 20 mg/kg body weight of the mammal.

7. The method of claim 6, wherein 3-hydroxy-dibenzo-alpha-pyrone is administered orally, intramuscularly, parenterally or transdermally.

8. The method of claim 6, wherein the mammal is a human, a dog, a horse, or a cat.

9. The method of claim 6, wherein body weight is decreased at least about 5%.

10. The method of claim 6, wherein body weight is decreased at least about 10%.

11. A method for preventing body weight gain comprising:
    identifying a mammal in need of such treatment experiencing weight gain; and
    administering to the mammal in need of such treatment an effective amount of 3 hydroxy-dibenzo-alpha-pyrone;
    wherein 3-hydroxy-dibenzo-alpha-pyrone is present in a daily dosage of from about 0.2 mg/kg body weight of the mammal to about 20 mg/kg body weight of the mammal.

12. The method of claim 11, wherein 3-hydroxy-dibenzo-alpha-pyrone is administered orally, intramuscularly, parenterally or transdermally.

13. The method of claim 11, wherein the mammal is a human, a dog, a horse, or a cat.

14. The method of claim 11, wherein body weight gain is decreased at least about 5%.

15. The method of claim 11, wherein body weight gain is decreased at least about 10%.

16. The method of claim 11, wherein body weight gain is decreased at least about 20% after administering a daily dosage of about 10 mg/kg body weight for about 4 weeks.

\* \* \* \* \*